United States Patent [19]
Ray

[11] Patent Number: 5,201,704
[45] Date of Patent: Apr. 13, 1993

[54] METHOD OF MAKING AND USING A HEMOSTATIC AGENT APPLICATOR

[76] Inventor: Joel W. Ray, 6367 Alvarado Ct., Suite 304, San Diego, Calif. 92120

[21] Appl. No.: 704,343

[22] Filed: May 23, 1991

Related U.S. Application Data

[63] Continuation-in-part of Ser. No. 432,906, Nov. 7, 1989, abandoned.

[51] Int. Cl.⁵ .............................................. A61B 17/56
[52] U.S. Cl. ...................................... 604/49; 604/286
[58] Field of Search ............... 604/358, 362, 367, 286, 604/49; 606/196

[56] References Cited

U.S. PATENT DOCUMENTS 3,566,871 3/1971 Richter et al. ...................... 128/296
3,837,950 9/1974 Reimels .................................. 156/73
4,338,941 7/1982 Payton ................................. 606/196

Primary Examiner—Michael H. Thaler
Attorney, Agent, or Firm—Wolf, Greenfield & Sacks

[57] ABSTRACT

An applicator for applying a hemostatic agent for use in achieving hemostasis in surgery comprises an absorbent material which has an attached removal string and radi-opaque localizer, and a mass of hemostatic agent interengaged with the material on at least one side. In the disclosed embodiment, the applicator is used by applying the material and hemostatic agent against an open, broken, bone surface, which is oozing blood. The hemostatic agent on the material is forced into the porous, bleeding bone to stop the bleeding, and the material is then removed and discarded. Hemostatic agents applied in this manner allow hemostasis of various oozing tissues.

5 Claims, 3 Drawing Sheets

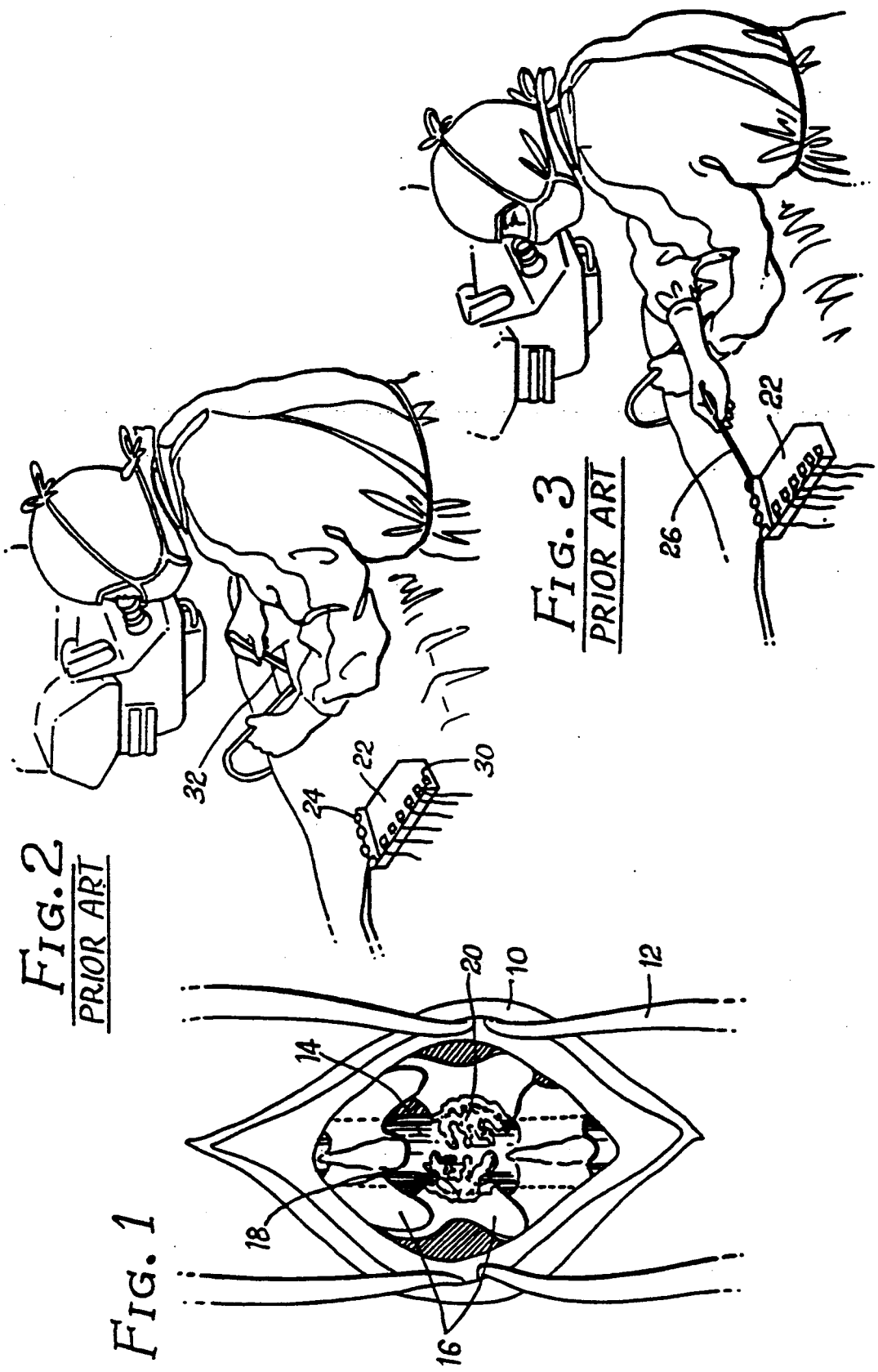

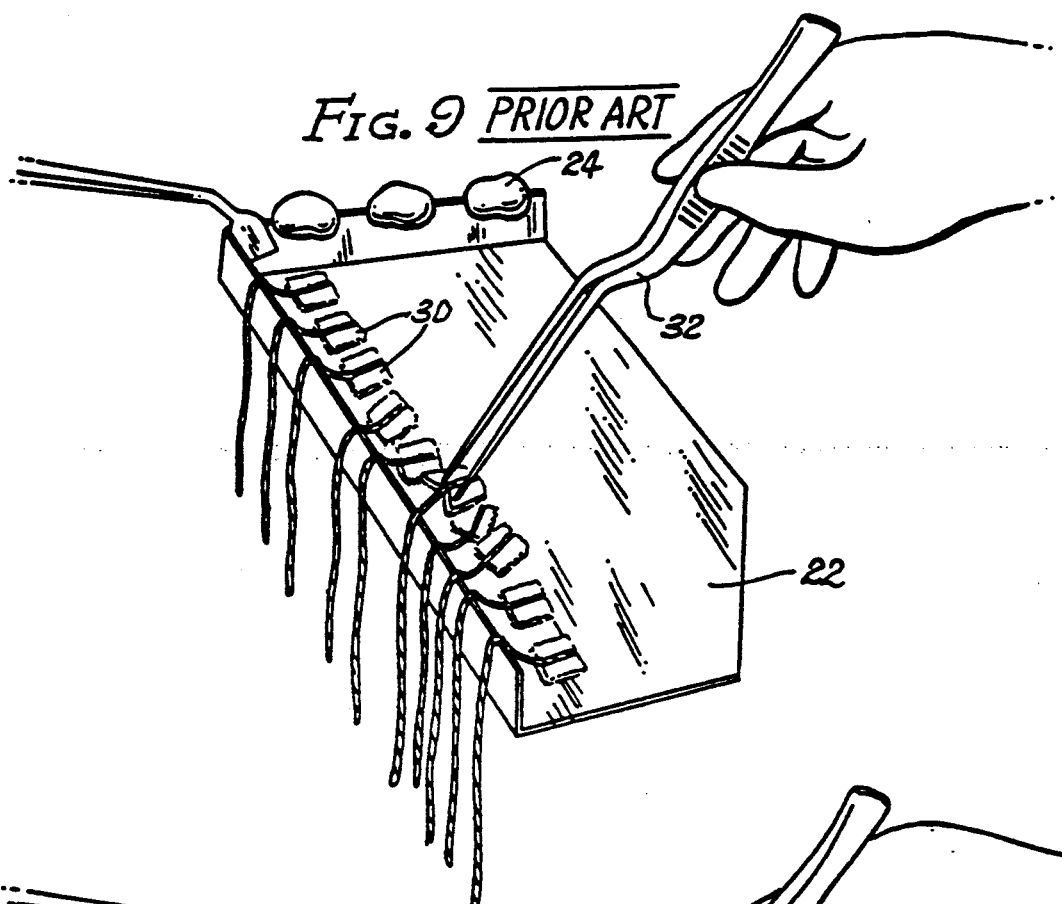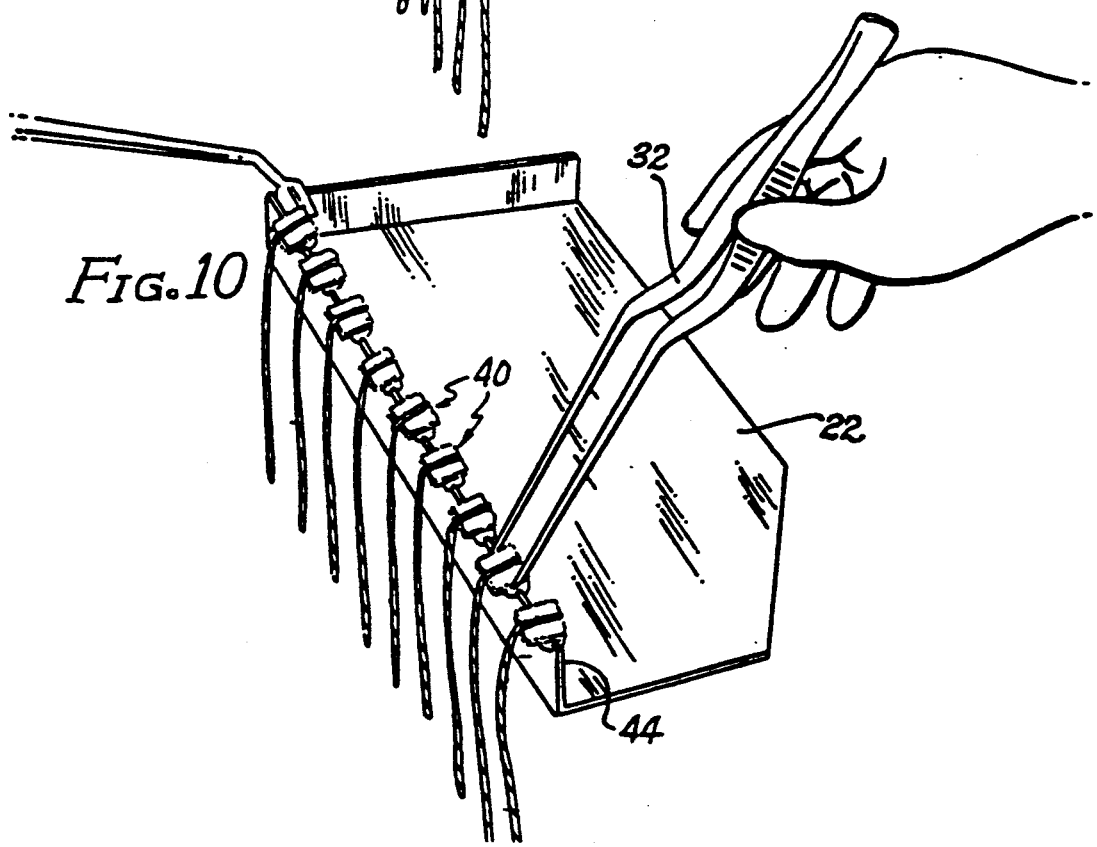

METHOD OF MAKING AND USING A HEMOSTATIC AGENT APPLICATOR

The present application is a continuation-in-part of application Ser. No. 07/432,906 entitled "Hemostatic Agent Applicator for Surgical Procedures" filed Nov. 7, 1989, now abandoned.

FIELD OF THE INVENTION

The invention relates to methods and materials for obtaining surgical hemostasis of oozing tissues, and more particularly obtaining hemostasis by the use of bone wax engaged with an applicator.

BACKGROUND OF THE INVENTION

In some surgical procedures, a particularly good example of which involves operations on the spinal cord, bone is broken away to provide access to the area requiring surgery. Where the bone has been broken, the remaining bone has open, porous areas and these areas typically ooze blood. Bone hemostasis is required to allow clear visualization of the surgical site by the surgeon during the operation, and also to prevent post-operative complications from blood accumulation.

During any surgery, it is necessary to stop blood ooze, or adsorb the blood, as best as is possible. With the major advances in microsurgery, even small amounts of blood provide intolerable obstructions in the surgeon's confined microscopic field of view. Because the microscopic field of vision during these operation has become increasingly confined, distractions of the surgeon from the immediate surgical field cannot be tolerated.

The tissue structures involved in microsurgery are extremely delicate, and even small amounts of blood obscure the anatomy. For surgery to proceed without unacceptable injury requires perfect clarity of vision. In a spinal operation, for example, the oozing bone is proximate to the very delicate neural structures. Stopping the ooze from the irregular surfaces is difficult and the surface must be filled with a compressing material to stop the bleeding. The technique to compress material into the bone surface requires a great deal more force than can be tolerated by the adjoining vulnerable neural structures, which are at risk with even the most careful techniques. Thus, a slip during bone hemostasis could be fatal. Preserving the vital structures while obtaining the required visualization warrants the utilization of the most advanced and delicate techniques. Simplifying the procedures and reducing the number of steps as much as possible is very important.

In microsurgical techniques, the surgeon is isolated from an ability to interact with the instrument field. There is very limited access to the microscopic field, also limiting the help available from assistants. The surgeon has come to depend on his own hands to provide the speed and efficiency needed to accomplish the highly delicate tasks of the microsurgical operation. Procedures which decrease the number of steps are critical to furthering the ability to accomplish microsurgery advances. Those which decrease the number of instruments to accomplish a maneuver are equally critical.

The health of the patient is also a factor. With advances in the understanding of infection and wound healing, incisional blood accumulation has become a known risk factor, and must be minimized. Medullary bone ooze is a major source of incisional bleeding in many surgical procedures.

Bone wax has been utilized since the late 1800's as an effective bone hemostatic agent. Typically, a metal instrument such as a spatula is used to bring a mass of bone wax from the surgical tray into the situs of the surgery, where it is pressed into the open bone; in effect sealing off the bleeding surface. Given the often irregular oozing surface, the metal instrument often proves to be too rigid, and a more conforming gloved finger may be used. Even a finger, however, often proves inadequate to conform the bone wax to bone spicules. Additionally, glove puncture may occur, exposing the surgeon and the patient to cross infection, not only from bacteria and hepatitis, but AIDS and other infections as well. Furthermore, the nurse or other operating room assistant must first manipulate the bone wax into a size that can be inserted into the situs of the operation. The resulting wax pieces are of inconsistent size, softness and texture.

Other bone-conforming interfaces, such as cotton materials, have been used, to attempt to force the bone wax evenly into the irregular bone surface. However, bone wax will not stick to wet cotton fibers. Furthermore, use of additional materials requires additional steps during the surgical procedure and also introduces an additional source of imprecision in the handling of the bone wax.

Although a nurse provides as much assistance as possible to the surgeon during the surgery, to achieve bone hemostasis the surgeon still must generally move one hand from the incision to a tray where the bone wax, and separately cotton sponges, have been placed by the nurse. Although, ordinarily, the doctor would not take his eyes off the incision, in some cases, that might also be necessary. It is critical that the surgeon keep his eyes steadily on the incision, and have both hands free to perform the operation, as much as possible. As the surgical procedures become ever more precise and taxing to the surgeon, and limit the ability to use an assistant in the small, critically delicate areas of operation, efficiency and simplicity of movement become of paramount importance. Reduction in the number of steps of surgery is thus requisite to advances in microsurgery.

SUMMARY OF THE INVENTION

The invention is a hemostatic agent applicator and a surgical method for reducing the operation time and the number of steps required of the surgeon to effectively reduce blood oozing. The ability to perform rigorous, demanding, tedious and high-risk operations in an extremely confined operative field is thus enhanced.

The applicator comprises a flexible absorbent material containing a mass of hemostatic agent integrally attached to the material for application to a variety of different tissue types. The absorbent material is preferably fibrous and contains interstitial spaces for engagement with the hemostatic agent. Preferred hemostatic agents are used for different tissue types. For example, Gelfoam TM is an absorbable gelatin, and Helistat TM and Avitene TM are collagen preparations which are applied to oozing soft tissue. Oxycel TM is an oxidized cellulose product used to achieve hemostasis. All of these products could be incorporated into the invention. A particularly preferred hemostatic agent is bone wax.

A method of manufacturing an applicator of the invention is also described. The method involves selecting an appropriate absorbent material and integrally attaching a hemostatic agent to the material by applying the agent in fluid form at or below the surface of the dry material so that the agent interengages with the interstices of the absorbent material. The agent is allowed to solidify. In another method of manufacture, heat and pressure are used to soften the hemostatic agent and force it into integral attachment with the absorbent material.

A particularly good example of an operation requiring hemostasis, and the example that is described and illustrated herein, is a spinal cord operation in which hemostasis of oozing bone must be achieved. The hemostatic agent used to arrest bone ooze in this operation is preferably bone wax.

The method uses the apparatus of the invention, a dry absorbent material made of cotton or the like which has a mass of hemostatic agent integrally attached to one surface. The absorbent material is used as an applicator, and in combination with the integrally attached hemostatic agent is preferably made wet and then inserted in the situs of the operation with the hand, or with forceps, or another surgical instrument. The hemostatic agent is applied by manipulating the absorbent material to push the mass against the oozing bone. The result reduces the steps in obtaining bone hemostasis because the surgeon needs to reach for and place only one object, the absorbent applicator with integrally attached bone wax, rather than two separate objects (an absorbent material and a separate mass of dry bone wax). As this may be done quite a number of times in a single operation, the applicator with integrally attached bone wax is a crucial advantage to surgeons, and particularly those surgeons who often perform microsurgical procedures.

Using the preformed applicator instead of loose balls of dry bone wax, the nurse lays out a series of applicators, ready for use on the surgical tray. The surgeon's and nurse's time are thus conserved, and attention to the operation is diverted less. The bone wax can be applied to the oozing bone in a superior fashion that insures closer adherence of the bone wax to the bone surface, and its even impregnation into the pores of the bone to achieve hemostasis.

Dry absorbent material containing integrally attached bone wax is arrayed on a tray and moistened prior to application to avoid damage to the spinal cord caused by contact with dry material. Bone wax will not adhere to an already wet surface, so that, in conventional procedures, the nurse would have to access an inventory of dry absorbent materials, further complicating the surgery. With pre-manufactured applicators, placement of the bone wax on a dry absorbent material is uniform and correct, and does not require the nurse's time or distraction from the surgeon or the operative field. The surgeon would be certain, in demanding and high-risk situations, of a ready supply of applicators with a known, uniform amount of appropriately placed bone wax.

BRIEF DESCRIPTION OF THE DRAWING

FIG. 1 is a diagrammatic illustration of a typical surgical incision in which the covering tissue has been parted to reveal the spinal column, and a portion of the spine has been broken away to provide the surgeon access to the spinal cord itself;

FIG. 2 is a diagrammatic illustration of a surgeon performing a demanding microsurgical operation within a confined operative field;

FIG. 3 illustrates the performing surgeon according to prior art techniques, securing a ball of bone wax, and separately a cotton sponge;

FIG. 9 illustrates a tray layout according to prior art techniques, requiring picking up absorbent material and bone wax separately;

FIG. 10 illustrates a tray prepared for surgery according to the method of the invention.

DETAILED DESCRIPTION OF THE PREFERRED EMBODIMENT

Figure 4:
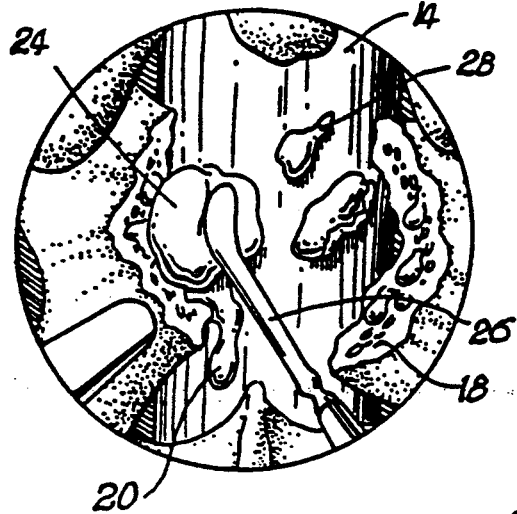
FIG. 4 illustrates the prior art technique of attempting, to maintain bone wax on a surgical spatula and press the bone wax into an irregular bone surface.

The applicator comprises a combination of a dry absorbent material and an applied hemostatic agent. As used herein, the term "absorbent" refers to natural and/or synthetic flexible materials that can pick up water or other liquids from various portions of the body. Specifically, the absorbent material can pick up and remove body fluids such as blood, serum, plasma, lymph, spinal fluid, tissue fluid, urine, sweat, bile juice and digestive juice. The absorbent material preferably contains interstitial spaces. For example, the absorbent material can be a sponge containing a plurality of pores capable of absorbing liquid. These sponges can be made of plastic or polymer compositions such as polyurethane foam and the like. Preferably, the absorbent material is a cottonoid material with interstices, which material is made of a plurality of synthetic or natural fibers. The term "cottonoid" is also meant to include fabric materials made of cotton or rayon, see, for example, U.S. Pat. No. 3,857,950, incorporated herein by reference, as well as gauze pads consisting of synthetic and/or natural fibers.

The hemostatic agent that is in combination with the absorbent material can vary depending on the different tissue type and purpose for which it is used. Hemostatic agents that are well-known to those of ordinary skill in the art are included within the scope of this invention. Preferred agents include Gelfoam TM, an absorbable gelatin; Helistat TM and Avitene TM, collagen preparations applied to soft oozing tissues; and Oxycel TM, an oxidized cellulose product used to achieve hemostasis. A particularly preferred hemostatic agent is bone wax.

The bone wax applicator and its technique of use are applicable to any surgical procedure in which bone is broken or injured, and bone hemostasis must be achieved, such as neurosurgery (cranial, spinal, peripheral nerve), orthopedics, eye, nose and throat surgery, and the like. The operation illustrated in the drawings is one in the region of the spinal cord. FIG. 1 diagrammatically illustrates the situs of the operation as it appears once the overlying tissue 10 has been cut, and held open by retractors 12 to expose the spinal column. The spinal cord 14 resides inside the vertebrae 16. In the illustrated operation, a portion of one vertebra has been removed to expose the spinal cord itself, creating open, spiculed bone surfaces 18. These surfaces will continue to ooze blood, indicated at 20, tending to obscure and clutter the area of the operation. It is critical that the bleeding be stopped or at least abated considerably so that the surgeon can perform the very fine techniques needed in miorosurgery.

The prior art technique of applying bone wax to the bone surfaces is illustrated in FIGS. 2 through 5, and 9. Typically, bone wax is laid out on the surgical tray 22 in the form of small globules or balls 24 that are broken off from a main mass of bone wax and kneaded into the proper consistency and size. There is no standardized or easily implemented manner of forming the bone wax globules. Although nurse assistance might be used, it may be easier and more expedient for the surgeon to reach over and secure a mass of bone wax on the end of a spatula 26, or secure the wax with another surgical instrument. The surgeon's attention, however, is diverted from the operation in order to engage the bone wax, as shown in FIG. 3. Although this is highly undesirable, nonetheless it is generally the most expedient method of getting the bone wax securely onto the bleeding bone.

Once the bone wax is in the incision, the surgeon's next procedure is to press it into the open bone surface as shown in FIG. 4. Because the spatula defines an unyielding applicator surface, it cannot conform to the surface of the bone 18, and pressing the bone wax into the bone in an attempt to achieve hemostasis is an awkward procedure. Fragments of wax may separate from the main mass, as shown at 28 in FIG. 4.

Once the bone wax is at least partially adhered to the bone surface, the surgeon may use a surgical sponge 30 engaged in forceps 32, in an attempt to more closely conform the wax to the surface, and to smooth it out over the entire oozing area and press it into place. The flexible nature of the sponge permits it to conform to the surface. At this point, however, the sponge is wet, having been moistened prior to the surgery, so that the wax will not stick to it.

It will be noted that the surgeon has now had to divert his attention twice, once to get the bone wax and then to get the sponge. This procedure would need to be duplicated for each open bone surface, adding up to a considerable number of times that the surgeon, for a few moments, could not observe the situs of the operation.

The overall operating risk is thus increased, due to three factors. First, the number of steps in the operation are increased. Second, valuable time is unnecessarily consumed. And, lastly, visual distraction of the surgeon increases the risk of incorrect movements and damage to vital tissues. Microsurgical cases require the minimization of the time required for the surgeon to hold a given, awkward position and to mitigate the overall tediousness of the exhausting, critical procedures. Unnecessary steps increase the number of hands required to accomplish these tasks in the extremely restricted field of operation. This leads to an increased risk of surgical misadventure when working in an unduly cluttered field.

As any surgeon is aware, any technique or product which reduces the necessary time that the hands or eyes of the surgeon are away from the operation are perceived as highly advantageous. Because of the extreme delicacy and complexity of some microsurgical operations, every assist available to the surgeon enhances the likely success of the operation.

Figure 6:
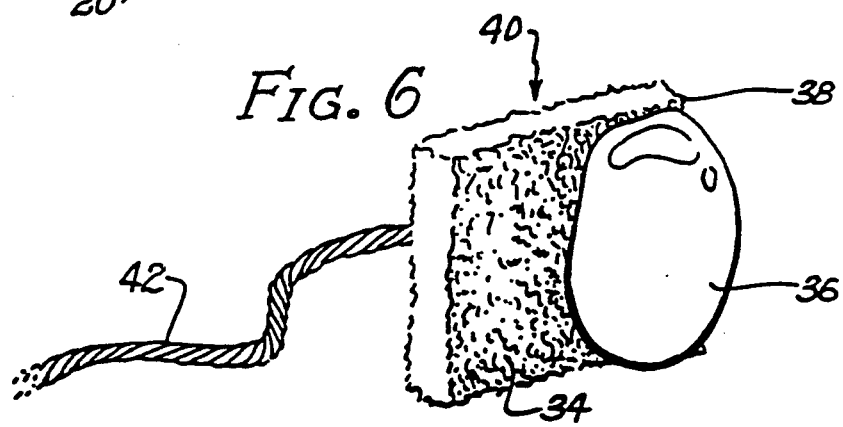
FIG. 6 is a perspective view of the applicator disclosed herein.

The applicator for applying hemostatic agent is illustrated in FIG. 6. It comprises an absorbent material preferably having interstitial spaces, such as a sponge 34, with a mass of bone wax indicated at 36 integrally attached to one surface of the absorbent material. As used herein, the term "integrally attached" refers to attachment of hemostatic agent to the absorbent material while dry under conditions sufficient to ensure an attachment of the hemostatic agent mass to the absorbent material in a manner that will not permit inadvertent detachment of the hemostatic agent from the material prior to use The hemostatic agent is integrally attached to a surface of the absorbent material or it can penetrate to some depth below the surface of the material. Preferably, this term is meant to include the interengagement of the interstices of the absorbent material with the hemostatic agent.

This interengagement may be achieved in several ways. For example, a known amount or volume of the hemostatic agent (e.g. bone wax) may be applied in highly softened or fluid form through hypodermic syringes or the like at a point below a surface of an absorbent material (e.g. a cottonoid) so that the fluid bone wax intimately interengages the cottonoid fibers at at least one surface of the cottonoid and projects from around those fibers upwardly of the cottonoid on one side. The fluid material is then allowed to solidify into a globular or ball-shaped mass. This combination of bone wax mass and cottonoid is shipped in dry form where it is subsequently wet for application, as described below.

Alternatively, various combinations of heat and pressure can be applied to malleable or soft bone wax in order to force the bone wax into interengagement with the interstices of the absorbent material (e.g. cottonoid). This combination of dry cottonoid and integrally attached bone wax mass is then wet and used by the surgeon. A water bath pre set to a temperature sufficient to melt or soften the bone wax is used as part of the operating room protocol. This water bath serves to both soften the bone wax on the absorbent material and wet the combination of bone wax and absorbent material.

The shape and sizes of the integrally attached bone wax and the absorbent material will vary depending on the particular use. Absorbent materials can include rayon and cotton squares ranging from about ¼ inch (6.3 mm) to about 3 inches (76.2 mm) on a side and upwards of about 0.04 inches (1 mm) in thickness. Thus, in brain surgery small components may be used such as absorbent squares ¼" or ½" on a side. With pelvic, leg or arm surgery, much more massive components may be used and the cottonoid material may be on the order of centimeters or tens of centimeters. A bone wax mass may project as a uniform layer over the absorbent material surface or, preferably, as a globular form above a surface of a cottonoid to a depth of several millimeters. A typical globule size can be ½ inch ×¼ inch ×1/16 inch (12.7 mm ×6.3 mm ×1.5 mm).

Figure 5:
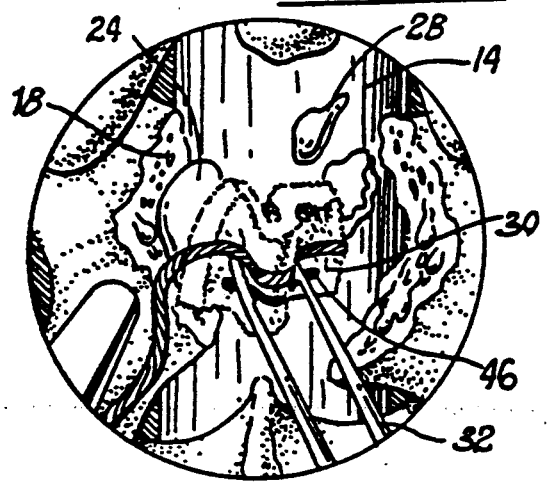
FIG. 5 illustrates a subsequent attempt by the surgeon to secure the bone wax in place by using a small surgical sponge.
Figure 7:
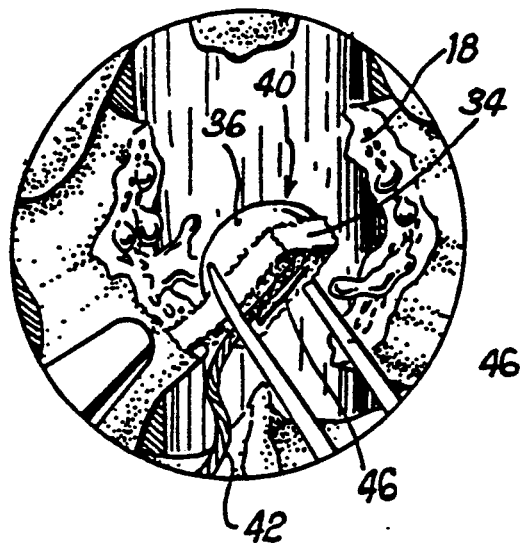
FIG. 7 illustrates the applicator in use, applying a mass of bone wax onto a bone surface.
Figure 8:
FIG. 8 illustrates a continuation of the procedure of FIG. 7 in which forceps press the flexible absorbent material with integrally adhered bone wax to conform the applicator to the irregular surface of the bone.

A globular shape of bone wax 36 attached to a portion of distal end 38 of the absorbent material (FIG. 6), as opposed to a uniform bone wax layer covering the entire surface of the absorbent material, enhances the ability of a surgeon to apply the bone wax under pressure to the bone surface. The portion of the absorbent material not covered by bone wax is engaged by the fingers or appropriate forceps, as illustrated in FIG. 7. Finally, the applicator 40 includes a removal string 42 of polyester fiber or other plastic material (e.g. nylon, polypropylene) attached to its surface on a side opposite the bone wax 36, and a radiopaque marker strip 46 as shown in FIGS. 5, 7 and 8. Attachment of a string to the back of the absorbent material is accomplished by adhesive techniques which are light enough so that the flexibility of the absorbent material is not jeopardized. Whereas the bone wax or other hemostatic agent is implantable and is left in the incision when it is closed, the absorbent material must be removed, and is therefore required to have a radiopaque marker. Numerous radiopaque materials well known to those of ordinary skill in the art can be used. Vinyl with barium sulfate dispersed therein is a commonly used marker.

The surgical technique of achieving hemostasis is now illustrated using the applicator of the instant invention, as shown in FIGS. 7, 8 and 10. FIG. 10 illustrates a layout of the applicators in preparation for a surgeon. The bone wax masses are conveniently pressed onto the edge 44 of the tray, allowing the surgeon to engage them with the forceps 32 without the applicators moving around on the tray while the surgeon tries to pick them up. The combination of bone wax and cottonoid is made using one of the procedures previously described under dry conditions. Immediately prior to use, the combination of dry cottonoid and integrally attached bone wax is then wet using, for example, sterile water or physiologic saline. The combination is then arrayed on a surgical table as illustrated in FIG. 10, supra, and used in wet form as desired.

In a single movement, the surgeon engages an applicator with the bone wax in place, and inserts it into the incision as shown in FIG. 7, where it is pressed against the bone surface as shown in FIG. 8. The fact that the bone wax was adhered in dry form to the absorbent material 34 before being applied to the bone lessens the tendency of the wax to fragment and fall away from the bone surface as was mentioned in reference to FIG. 4. The flexible absorbent material is then manipulated to press the mass of bone wax against the bone surface and will substantially conform to all of the irregularities of the bone surface, as shown in FIG. 8. Once the bone wa is securely pressed into all of the open bone structure, the applicator is removed from the situs of the operation and discarded. An amount of hemostatic agent is thus displaced from the surface of the absorbent material and remains at the situs of the operation.

The surgeon will repeat this technique a number of times, each time saving at least one step over the prior art technique, as he must only divert his attention once for each open bone surface that is treated.

The applicators would ordinarily be provided preformed and pre-packaged, and made available to the operating room nurse in a form convenient for removal and arrangement on a surgical tray, facilitating access by the surgeon.

Summarizing, in advancing the ability to perform these delicate procedures, the improved applicator and its procedure for use provide the following advantages over previously used techniques:

1) The number of steps in surgery is decreased.
2) The instrumentation used by the surgeon is simplified.
3) The surgeon's ability to control the instrumentation is simplified.
4) The surgeon's time distracted from visualizing the operative field is minimized.
5) The diversion of the surgeon's hands from the operative field is reduced.
6) Preparation time of the assisting nurse is minimized.
7) Distraction of the nurse's attention from the surgeon's needs is minimized.
8) The overall operating time is substantially decreased.
9) The risk of glove puncture and consequent cross infection is reduced.

EQUIVALENTS

Those skilled in the art will recognize, or be able to ascertain using no more than routine experimentations, many equivalents to the specific embodiments of the invention described herein. Such equivalents are intended to be encompassed in the scope of the following claims.

I claim:

1. A method of achieving hemostasis of bone surfaces during surgery, comprising
   a) integrally attaching a dry flexible absorbent member to a solid mass of bone wax remote from said bone surface, said mass projecting from a surface of said absorbent member;
   b) applying said bone wax to an open bone surface;
   c) manipulating said flexible absorbent member to press said bone wax into the open bone surface to cover said surface; and
   d) removing said flexible absorbent member from the situs of the bone while laving a quantity of the bone wax in contact with said surface.

2. The method of claim 1, further comprising wetting said absorbent member and mass of bone wax with liquid prior to step b).

3. A method of making a hemostatic agent applicator for surgery, comprising the steps of:
   a) selecting a dry absorbent material having interstitial spaces and at least one surface;
   b) applying a hemostatic agent in fluid form to a point below the surface of said material remote from oozing tissue;
   c) allowing the fluid hemostatic agent to interengate the insterstices of said material and project from around the said surface outwardly;
   d) allowing the hemostatic agent to solidify, wherein the step of applying a hemostatic agent comprises applying bone wax.

4. A method of making a bone wax applicator for surgery, comprising the steps of:
   a) selecting an absorbent material having interstitial spaces and at least one surface;
   b) applying bone wax to said absorbent material remote from an operating situs under pressure sufficient to soften the bone wax and force said bone wax into interengagement with the interstices of the absorbent material, said material projecting outwardly from around the said surface.

5. The method of claim 4, wherein the step of selecting an absorbent material comprises selecting a fibrous cotton sponge.

* * * * *